Figure 4:
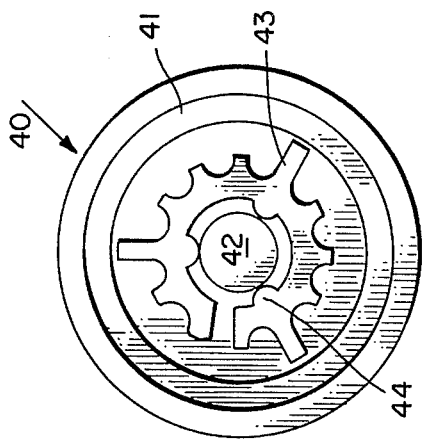

United States Patent [19]

Parsons

[11] 4,011,941
[45] Mar. 15, 1977

[54] CONTACT LENS CAPSULE

[75] Inventor: Frederick L. Parsons, Ridgewood, N.J.

[73] Assignee: Warner-Lambert Company, Morris Plains, N.J.

[22] Filed: Apr. 28, 1975

[21] Appl. No.: 572,551

[52] U.S. Cl. .................................. 206/5.1; 220/203
[51] Int. Cl.² ..................... A45C 11/00; B08B 3/04
[58] Field of Search ................ 206/5.1, 217, 204; 220/203, 366, 367; 251/DIG. 1; 137/525, 516, 15; 21/58, 83

[56] References Cited

UNITED STATES PATENTS

| 1,466,132 | 8/1923 | Lippert | 206/217 |
|---|---|---|---|
| 2,757,685 | 8/1956 | Fritsch | 220/203 |
| 3,113,579 | 12/1963 | Willis | 206/5.1 |
| 3,379,200 | 4/1968 | Pennell | 206/5.1 |
| 3,473,886 | 10/1969 | Leeds | 206/5.1 |
| 3,504,822 | 4/1970 | Haloski | 220/203 |
| 3,770,113 | 11/1973 | Thomas | 206/5.1 |
| 3,873,696 | 3/1975 | Randeri et al. | 21/58 |

Primary Examiner—William T. Dixson, Jr.
Attorney, Agent, or Firm—Albert H. Graddis; Frank S. Chow; George M. Yahwak

[57] ABSTRACT

An apparatus comprising a sterilizing capsule for the sterilizing of soft contact lenses in an aqueous hydrogen peroxide solution is disclosed.

15 Claims, 10 Drawing Figures

U.S. Patent   Mar. 15, 1977   Sheet 1 of 3   4,011,941

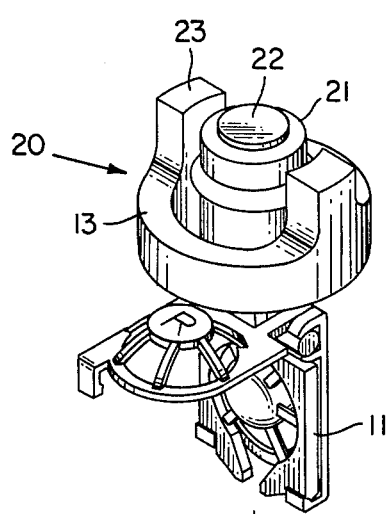

CONTACT LENS CAPSULE

A method for removing hydrogen peroxide from soft contact lenses which have been sterilized with hydrogen peroxide is disclosed in U.S. pat. application Ser. No. 454,141, the disclosure of which is incorporated herein, as an alternative to the method of sterilizing these lenses by boiling in an aqueous solution. This method comprises immersing the soft contact lenses in an aqueous system containing a decomposition catalyst which acts on the hydrogen peroxide to convert it to water and free oxygen.

In the above procedure an amount of 3% by weight of hydrogen peroxide containing sufficient sodium chloride to yield a 0.85% saline solution is introduced into a container comprising a cup, a contact lens basket, and a desired decomposition catalyst. The lenses are then allowed to remain in contact with the hydrogen peroxide solution for approximately 6 hours. After this time, the lenses are effectively sterilized and the concentration of hydrogen peroxide is reduced to about 20 PPM. To avoid possible discomfort, a single rinse in isotonic saline may subsequently be affected to reduce the hydrogen peroxide concentration to less than 10 PPM, an amount which can be readily tolerated in the eye.

In the present invention, a sterilizing capsule having the characteristics to be herein described is highly effective in carrying out soft contact lens sterilizing procedures using a hydrogen peroxide decomposition catalyst system.

Accordingly one object of the present invention is to provide an improved capsule for use in a hydrogen peroxide sterilizing procedure for affecting the sterilization of soft contact lenses.

Another object of the present invention is to provide an improved sterilizing capsule which is sealed to contain the sterilizing solution but which allows the oxygen produced during the hydrogen peroxide decomposition reaction to escape.

The exact manner in which these and other objectives of this invention are achieved will become apparent when references made to the following detailed description of the preferred embodiments of the invention and to the accompanying drawings in which like reference numerals indicate corresponding parts throughout the several views of the drawings.

Figure 2:
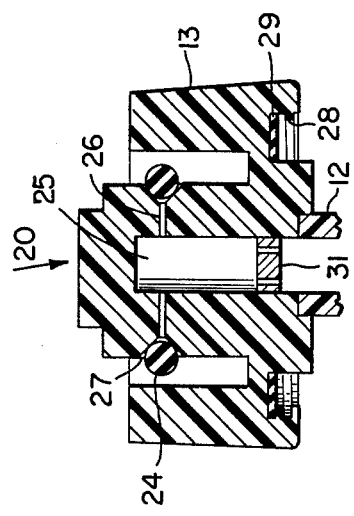
Figure 3:
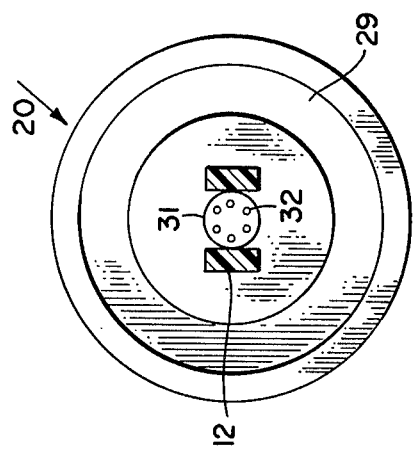
Figure 1:
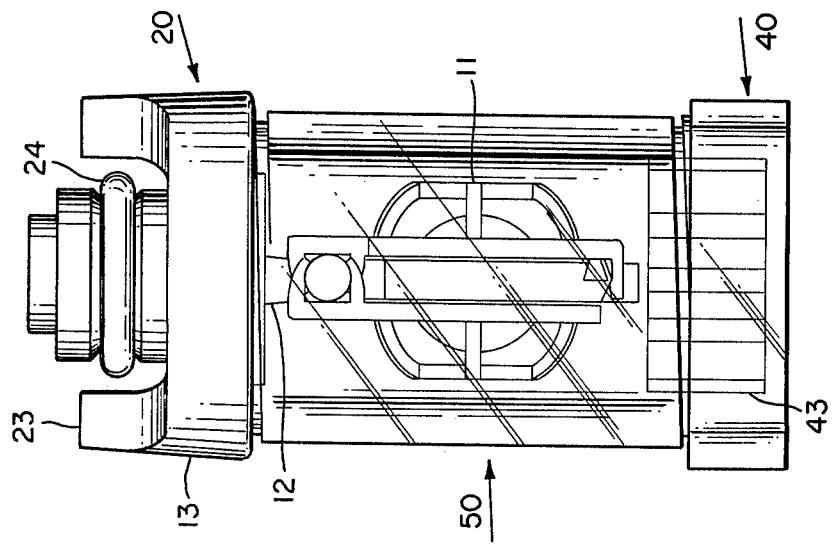
Figure 9:
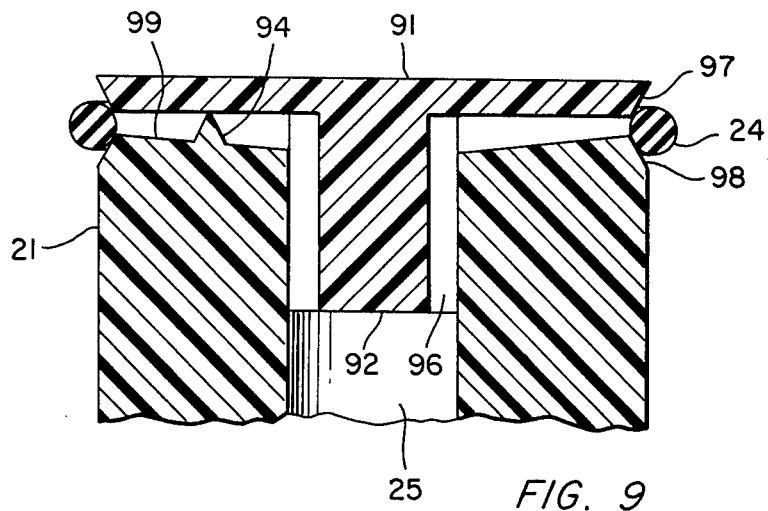
Figure 10:
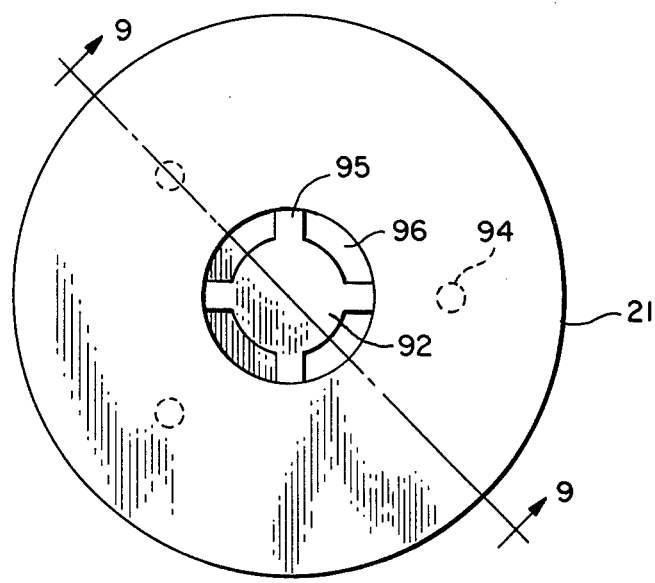

In the drawings:
FIG. 1 is a side elevational view of the assembled capsule;
FIG. 2 is a vertical cross sectional view of the upper cap of the capsule;
FIG. 3 is a view of the base of the upper cap;
FIG. 4 is a plan view of the lower cap of the capsule;
FIG. 5 is an exploded perspective view of the capsule according to the present invention;
FIG. 6 is a vertical cross sectional view of a modified form of the upper cap;
FIG. 7 is a view of the base of the cap of FIG. 6;
FIG. 8 is a vertical cross sectional view of another modified form of the upper cap;
FIG. 9 is a vertical cross sectional fragmentary view of the upper cap of FIG. 10 taken along line 9—9;
FIG. 10 is a plan view of the upper surface of a cap having a modified central post structure.

Referring to the drawings and specifically to FIG. 1, the sterilizing capsule of my invention consists of a hollow cylindrical body 50 having male screw threads 51 on each end thereof which carry a bottom cap 40 and an upper cap 20. The female screw threads 45 of the bottom cap capable of engaging the threads at one end of the body with the connection being sealed by a gasket 41 located at the base of cap 40. This construction produces a water proof seal when the bottom cap is tightened against the piece of body 50. The bottom cap also carries a vertical disposed axial post 42 on which is mounted a convoluted catalytic reactor 43 which is held to this central post by friction. The preferred catalytic material is a surface layer of platinum black which has been deposited on a molded substrate of the desired shape. The substrate is molded in the form of a split ring provided with inner gripping means 44 which grip the central post for a friction fit.

In order to support the contact lenses during sterilization, a lens basket 11 is attached by means of a support post 12 to the inner surface of the upper cap by any conventional method such as the use of adhesives, friction or snap fittings, or alternatively, the support posts may be molded as part of the upper cap.

The upper cap 20 comprises as shown in FIGS. 1 and 2 an outer circumferential collar 13 and spaced inwardly thereof, a central post 21 extending upwardly along the central axis of the cap and terminating in a flat top surface 22. The collar may be shaped to form raised portions along a common diameter of a cap defining wings 23 to aid in gripping the cap when attaching and detaching it from the body 50. The female screw threads 28 of the cap are adapted to engage the corresponding male threads on the body 50 and thereby allow the two units to be connected. The upper cap is also provided with a gasket 29 which produces a water proof seal when the cap is firmly attached to the body.

An axial core opening extends from the inner base of the cap into an axial core cavity 25 extending upward into the post a distance short of the flat top. This cavity connects with radial openings 26 which extend through the central post to the apex of a truncated conical annular groove 27 extending circumferentially about the post. A flexible seal 24 in the form of an elastic O-ring fits into this groove and the pressure asserted by the flexible seal against the annular groove affords a liquid proof seal which prevents any liquid contained in the body of the assembled capsule from escaping.

A core opening restriction means is located at the core opening in the base of the cap, and may comprise a disc 31 provided with perforations 32, a baffle means having channels as shown in FIGS. 7 and 10, or a venturi constriction as shown in FIG. 8.

In use the soft contact lenses are placed within the basket and the upper cap carrying the basket is firmly attached to the open cylindrical body. Hydrogen peroxide sterilizing solution is then poured into the open end of the capsule until the lenses and basket are immersed. The capsule is then sealed by attaching the lower cap carrying the catalyst. The capsule is then allowed to remain inverted to allow the hydrogen peroxide to act without being in contact with the catalytic reactor. After the desired period of sterilization is completed, the capsule is inverted so that it now rests upon the base of the lower cap and the hydrogen peroxide is in contact with the catalytic reactor. During sterilization, the O-ring seal will prevent the solution from leaking out of the capsule. At the end of the sterilization, when the capsule is reversed, the hydrogen peroxide solution comes in contact with the catalyst which acts to decompose the hydrogen peroxide to form water and oxygen.

As the pressure of the oxygen formed within the capsule increases, the seal formed by the O-ring acts as a pressure release valve and the oxygen is thus allowed to escape.

A modified form of cap 60 as shown in FIG. 6 comprises a cylindrical collar 13 having an inner annular flange 65 through which a separate detachable inner post 66 is passed. This post is cylindrical in shape and has a core opening, a core cavity, radial openings, female threads, and a gasket as previously described. The detachable post is of a diameter sufficient to fit within the central opening of the collar's annular flange; the post itself has a radially extending circumferential flange 64 having a diameter to cooperatively fit into the cavity defined by the female threads of the collar and to abut the annular flange. The core opening within the post carries a cylindrical solid baffle 62 having a spacing tab 63 which effectively limits the baffle at a sufficient distance below the radial openings to form the core cavity. The longitudinal surface of the baffle is grooved to form a series of annular channels 71 communicating with the core opening and the core cavity. A tab 61 extends from the baffle in opposite direction to the space tab and carries a basket support structure. The unit is assembled by inserting the detachable post into the central opening of the annular flange until the circumferential flange abuts the annular flange of the collar assembly. The gasket is then positioned about the lower perimeter of the post flange thus assuring a water proof seal when the cap is firmly attached to the body.

FIG. 8 shows another modified cap 80 having a detachable central post 85. The collar 81 in this modification is elongated to extend a greater distance than the post when the cap is assembled and thus the collar's upper surface forms a surface upon which the unit rests when inverted and the lenses are being sterilized. The inner surface of the collar includes an inwardly extending stop means 82 located at the base of the female screw threads 83 and capable of abutting the flange 84 extending outwardly from the central post and spaced along the length of the post, thereby limiting the post within the collar when the cap is assembled. The core opening 86 of the central post is a venturi-like constriction, generally a truncated conical bore, which terminates at the core cavity.

The modified central post in FIG. 9 does not contain radial openings through the post, but terminates in a top surface 99 which tapers centrally from the perimeter of the post to the core cavity. Spacing means 94 located either on the upper surface of the post as shown, or on the lower surface of the flat discoidal cover 91, space the cover at a distance from the upper surface of the post when the cap is assembled. The cover has an axial downward extending post 92 of an outer diameter less than the diameter of the core cavity and carries guiding and spacing ribs 95, which cooperate with the surface of the cavity to position the post within the cavity and also to form longitudinal channels 96 which connect with the core opening and the space between the cover and post surfaces. The outer perimeter 97 of the cover is beveled centrally and downwardly and cooperates with the downwardly and outwardly beveled perimeter 98 of the upper post surface to form a truncated conical annular groove in which the O-ring seal is held.

Having described my invention, and the manner and process of making and using it in such full, clear, concise and exact terms as to enable any person skilled in the art to which it pertains to make and use the same, I claim:

1. A capsule for soft contact lenses which comprises:
    a hollow, cylindrical body of sufficient diameter to receive a pair of contact lenses;
    a detachable closure means for attachment to one end of the hollow body and able to form a water proof seal when attached to the body, and having a catalyst attached thereto;
    a second removable closure means for attachment to the other end of the hollow body and having at least one passageway extending therethrough and terminating at its outer end and in an annular truncated conical groove.

2. The capsule as defined in claim 1 wherein the first closure means further comprises:
    a screw cap having a central post extending along the inner central axis; and
    wherein the means for producing the water proof seal is a gasket.

3. The capsule as defined in claim 1 wherein the second closure means further comprises:
    a contact lens basket for receiving soft contact lenses in spaced apart relationship and for positioning said lenses within said cylindrical body;
    a flat planar top surface.

4. The capsule as defined in claim 3 wherein the second closure means further comprises:
    a screw cap having an outer cylindrical collar and spaced inwardly thereof an axial extending post.

5. The capsule as defined in claim 4 wherein said post is further defined in that:
    said flat planar top surface defines its uppermost end; said passageway extends from an inner surface opening in said cap into a cavity about the central axis of the post to a point less than the length of the post and at least one radial opening extending from the cavity and passing through the post; and
    a pressure responsive venting seal cooperating within the conical groove to seal the radial openings against liquids.

6. The capsule as defined in claim 5 wherein said opening has a restricting means to reduce the diameter of said opening prior to entering said cavity, and wherein the seal is an O-ring.

7. The capsule as defined in claim 5 wherein said central post is detachable from said upper closure means.

8. The capsule as defined in claim 4 wherein the passageway extends along the longitudinal axis of the post and terminates in a space defined by the upper surface of the post and the bottom surface of a flat discoidal cover held in spaced apart relationship to the post.

9. A capsule for sterilizing soft contact lenses, comprising; a cup for receiving the contact lenses and sterilizing medium; said cup having a base and means for holding said lenses within the cup; detachable closure means for sealing the cup against liquid flow; a catalyst internally attached to said detachable closure means so as to contact the medium only when the capsule is inverted; and valve means in said cup base communicating internally of the capsule for venting gases generated by action of the catalyst on the medium.

10. The capsule of claim 9 wherein the cup base comprises a second detachable closure having the holding means suspended therefrom and sealing the cup base against liquid flow.

11. A capsule of claim 10 wherein the cup is a cylindrical chamber, the closures are threadably engaged thereto, and a sealing member is compressively captured between the closures and a complimentary portion of the chamber to form a liquid seal.

12. The capsule of claim 6 wherein the valve means comprises a cylindrical member having at least one radially extending port communicating internally of the capsule, the port intersecting a co-planer external annular groove in which an O-ring is located, the O-ring having selected diameter and durometer so as to prevent liquid flow and allow venting of gas above a certain pre-determined pressure.

13. The capsule of claim 12 wherein the cylindrical member includes a plurality of ports, the groove is of a conical cross-sectional geometry, and it axially extends exteriorly of the second closure.

14. The capsule of claim 13 wherein the cylindrical member comprises:
- a first portion integrally formed with the second closure having an axial cavity extending therethrough;
- a second portion having a discoidal cover from which axially extends a post having a diameter complimentary with that of the cavity;
- the post containing exterior, axially extending channels over a portion of its length;
- a plurality of protuberences extending from the first portion top for spacing the discoidal member from the first member when the post is inserted within the cavity;
- the peripheries of both the discoidal member and the first member being inwardly chamfered to form the groove; and
- the channels and spacing communicating internally of the capsule for venting gases.

15. The capsule of claim 13 wherein the sterilizing medium is hydrogen peroxide and the catalyst is platinum black.

* * * * *